United States Patent [19]

Hausheer

[11] Patent Number: 6,077,838
[45] Date of Patent: Jun. 20, 2000

[54] METHOD OF TREATING HANGOVER

[75] Inventor: Frederick Herman Hausheer, Boerne, Tex.

[73] Assignee: BioNumerik Pharmaceuticals, Inc., San Antonio, Tex.

[21] Appl. No.: 09/327,736

[22] Filed: Jun. 8, 1999

[51] Int. Cl.[7] .................. A61K 31/66; A61K 31/095; A61K 31/105; A61K 31/10
[52] U.S. Cl. ................... 514/127; 514/129; 514/143; 514/706; 514/707; 514/709
[58] Field of Search ................... 514/127, 129, 514/143, 706, 707, 709

[56] References Cited

U.S. PATENT DOCUMENTS 4,220,660  9/1980  Brock .

*Primary Examiner*—William R. A. Jarvis
*Attorney, Agent, or Firm*—Thomas J. Dodd

[57] ABSTRACT

This invention relates to a method of treating patients afflicted with hangover. The method includes administering to a patient in need of treatment an effective amount of a thiol or reducible disulfide compound according to the formula set forth in the specification.

4 Claims, No Drawings

METHOD OF TREATING HANGOVER

FIELD OF THE INVENTION

This invention relates to methods of reducing or reversing the effects of hangover, and will have application to methods of reducing hangover that has been induced by consumption of alcohol or other intoxicants.

BACKGROUND OF THE INVENTION

The condition associated with morning after alcohol consumption, commonly referred to as hangover is often manifested by symptoms such as headache, fever, chills, nausea, muscle and nerve pain, lethargy, and others. While not a life-threatening condition, hangover can be very unpleasant, as well as detrimental on the job or at home. Unfortunately, hangover is a very common problem.

Currently, the most common method of treating hangover is rest along with self-administration of NSAIDs, painkillers, antacids, and other prescription and OTC drugs.

None of the current methods attacks the underlying cause of the symptoms, thought to be accumulation of alcohol metabolites in affected tissues. During sleep (often a byproduct of alcohol consumption, since alcohol is a CNS depressant), the body's metabolic processes slow, and may account for the incomplete metabolism/elimination of alcohol.

The rate at which the body metabolizes and eliminates alcohol and its metabolites varies greatly from person to person. This explains why some people suffer from hangover after only consuming a drink or two, while others can ingest large quantities and be unaffected the next morning. Some people eliminate alcohol at such a slow rate they may be affected for days after consuming only a small amount of alcohol.

Another factor to be considered in treating hangover is the social stigma associated with the condition. Despite the physiologic fact that some people simply do not metabolize alcohol to a significant extent, hangover in such people is often ridiculed and frowned upon. Further, hangover can adversely affect one's reputation especially if categorized as an alcoholic or the like.

Prior Medicinal Uses of Sulfhydryls and Disulfides

Mesna (sodium2-mercaptoethane sulfonate) and dimesna or (disodium 2,2'-dithiobis ethane sulfonate) are known therapeutic compounds that have heretofore demonstrated a wide variety of therapeutic uses. Both mesna and dimesna have been shown to be effective protective agents against certain specific types of toxicity associated with the administration of cytotoxic drugs used to treat patients for various types of cancer. In particular, mesna has been used with some success in mitigating the toxic effects of cytotoxic agents such as ifosfamide, oxazaphosphorine, melphalane, cyclophosphamide, trofosfamide, sulfosfamide, chlorambucil, busulfan, triethylene thiophosphamide, triaziquone, and others, as disclosed in U.S. Pat. No. 4,220,660, issued Sept. 2, 1980.

The near absence of toxicity of dimesna further underscores the usefulness of this compound, as large doses that may be needed can be given to a patient without increasing the risk of adverse effects from the protective agent itself.

Further, pharmacological profiles of each compound indicate that, if proper conditions are maintained, mesna and dimesna do not prematurely inactivate primary therapeutic drugs to a significant degree. Thus, neither compound will significantly reduce activity of the chemotherapeutic agent, and in many cases, act to potentiate the effect of the main drug on targeted cancer cells.

The structures of both mesna and dimesna are shown below as Formula I and Formula II respectively.

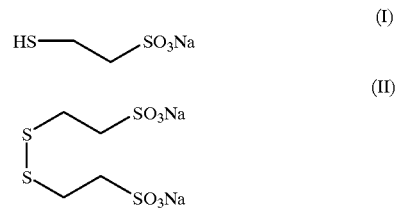

As is well known, dimesna is a dimer of mesna, with the optimum conditions for oxidation occurring in the slightly basic (pH~7.3), oxygen rich environment found in blood plasma. In mildly acidic, low oxygen conditions, in the presence of a reducing agent such as glutathione reductase, conditions prevalent in the kidneys, the primary constituent is mesna.

Mesna acts as a protective agent for a number of cytotoxic agents by substituting a nontoxic sulfhydryl moiety for a toxic hydroxy (or aquo) moiety. This action is particularly evidenced in the coadministration of mesna and oxazaphosphorine, and in the administration of dimesna along with cisplatin or carboplatin.

Mesna and dimesna, as well as some analogues of these compounds, have excellent toxicity profiles in mammalian species. In fact, dimesna has been administered intravenously to mice and dogs in doses higher than the accepted oral $LD_{50}$ for common table salt (3750 mg/kg), with no adverse effects. Dimesna has also been administered to humans in doses exceeding 15 $g/m^2$, with no adverse effects.

Mesna, and other analogues with free thiol moieties, constitute the more physiologically active form of the two types of compounds described in this specification. These compounds manifest their activity by providing free thiol moieties for terminal substitution at locations where a terminal leaving group of appropriate configuration is located.

Dimesna and other disulfides can be activated intracellularly by glutathione reductase, a ubiquitous enzyme, thereby generating high concentrations of intracellular free thiols. These free thiols act to scavenge the free radicals and other nucleophilic compounds often responsible for causing cell damage.

This profile is especially significant in explaining the success of dimesna in controlling and mitigating the toxic effects of platinum complex antitumor drugs. The mechanism for action in the case of cisplatin (cis-diammine dichloro platinum) is explained in U.S. Pat. No. 5,789,000, which is incorporated herein by reference.

Mesna, dimesna, and analogues of these compounds have been the subject of several prior pharmaceutical uses described in the literature and in prior patents, both in the United States and around the world. In addition to the cytotoxic agent protection uses, one or more of these compounds have proven effective, in vitro, against a multiplicity of biological targets, and have been effective, in vivo, in the treatment of sickle cell disease, radiation exposure, chemical agent exposure, and other uses.

Mesna, dimesna, and analogues thereof are synthesized from commonly available starting materials, using acceptable routes well-known in the art. One such method involves the two-step, single pot synthetic process for making dimesna and like compounds of the following formula:

$$R_1-S-R_2;$$

wherein:

R$_1$ is hydrogen, X-lower alkyl, or X-lower alkyl-R$_3$;

R$_2$ is -lower alkyl-R$_4$;

R$_3$ and R$_4$ are each individually SO$_3$M or PO$_3$M$_2$;

X is absent or X is sulfur; and

M is an alkali metal.

The process essentially involves a two step single pot synthetic process that results in the conversion of an alkenyl sulfonate salt or acid to the desired formula I compound. The process in the case of mesna is a single step process that converts the alkenyl sulfonate salt to mesna or a mesna derivative by reacting with an alkali metal sulfide or with hydrogen sulfide.

If the desired end product is dimesna or a dimesna analogue, a two-step single pot process is involved. Step 1 is as described above. Step 2 of the process is performed in the same reaction vessel as Step 1 without the need to purify or isolate the mesna formed during that step. Step 2 includes the introduction of oxygen gas into the vessel, along with an increase in pressure and temperature above ambient values, at least 20 pounds per square inch (psi) and at least 60° C. Dimesna or a derivative thereof is formed in essentially quantitative yield.

Other processes, well-known and documented in the prior art, may be employed to make either mesna or dimesna, or derivatives and analogues thereof.

SUMMARY OF THE INVENTION

This invention involves the administration of an effective amount of a compound of formula I, below, for treating patients suffering from hangover.

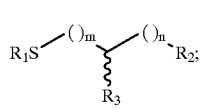

(I)

wherein:

R$_1$ is hydrogen, lower alkyl or

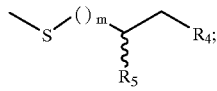

R$_2$ and R$_4$ are each individually SO$_3^-$M$^+$, PO$_3^{2-}$M$_2^{2+}$, or PO$_2$S$^{2-}$M$_2^{2+}$;

R$_3$ and R$_5$ are each individually hydrogen, hydroxy or sulfhydryl;

m and n are individually 0, 1, 2, 3 or 4, with the proviso that if m or n is 0, then R$_3$ is hydrogen; and M is hydrogen or an alkali metal ion; or a pharmaceutically acceptable salt thereof.

Effective amounts of the formula I compounds to be administered according to the method of this invention vary, and depend on the severity and duration of the hangover.

Accordingly, it is an object of this invention to provide for a method of safely and effectively treating hangover.

Another object is to provide a method of treating hangover by administration of a thiol or reducible disulfide to the patient in need of treatment.

Other objects will become apparent upon a reading of the following description.

DESCRIPTION OF THE PREFERRED EMBODIMENTS

The preferred embodiments herein described are not intended to be exhaustive nor to limit the invention to the precise form disclosed. They are chosen and described to explain the principles of the invention, and its application and practical use to best enable others skilled in the art to follow its teachings.

The method of this invention involves the administration of an effective amount of a formula I compound to a patient suffering from hangover. Administration may be either oral or parenteral.

The effective amount of the formula I compound will necessarily depend upon the degree of the hangover. Since the formula I compounds are essentially nontoxic, large amounts can be safely administered. The preferred dosage to treat hangover ranges from 0.1 mg/kg of body weight up to 3,000 mg/kg. The more severe the hangover and associated neuronal degradation, the more formula I compound should be administered to provide an effective response.

Administration is preferably through parenteral or oral routes. For parenteral administration, the formula I compound is dissolved in a suitable solvent, most preferably water, to produce a solution that may be injected. One or more pharmaceutically acceptable excipients may also be added to provide for an elegant formulation.

For oral administration, the formula I compound is preferably combined with one or more pharmaceutically acceptable excipients, fillers and/or diluents. Oral dosage forms may include pills, caplets, tablets, and others. Alternatively, the formula I compound may be contained in a swallowable container such as a gelatin capsule or the like.

The formula I compounds work to detoxify metal complexes or free radicals by substituting a thiol moiety for a toxic free radical or other nucleophilic moiety. In the case of hangover, the formula I compounds serve to alleviate the cause by rapidly eliminating the free radical moieties thought to be responsible for the condition.

Administration of the formula I compound should be made as soon as possible. Preferred initial dose is between 20 mg/kg and 500 mg/kg, and is usually a self-administered oral dose.

Other accepted methods of treatment may also be combined with the administration of the formula I compound. In particular, if the hangover is severe, NSAIDs, antacids or other drugs may be administered to alleviate symptoms while the formula I compound is circulating.

It is understood that the above description is in no way limiting of the invention, which may be modified within the scope of the following claims.

What is claimed is:

1. A method of treating a patient afflicted with hangover, said method comprising administering an effective amount of a compound of formula I:

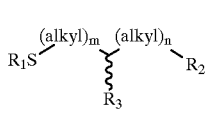

(I)

wherein:

$R_1$ is hydrogen, lower alkyl or

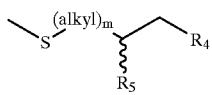

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof.

2. The method of claim 1 wherein the effective amount of the formula I compound administered is from 0.1 mg/kg of body weight to 1,000 mg/kg of body weight.

3. The method of claim 1 wherein the compound is administered orally.

4. The method of claim 1 wherein the compound is administered parenterally.

* * * * *